United States Patent [19]

Hou

[11] 4,348,476

[45] Sep. 7, 1982

[54] PRODUCTION OF EPOXIDES SUCH AS PROPYLENE OXIDE USING PACKED CATALYTIC BED CONTAINING MOIST RESTING CELLS EXHIBITING OXYGENASE ACTIVITY

[75] Inventor: Ching T. Hou, Edison, N.J.

[73] Assignee: Exxon Research and Engineering Co., Florham Park, N.J.

[21] Appl. No.: 227,135

[22] Filed: Jan. 22, 1981

[51] Int. Cl.$^3$ ............................................. C12P 17/02
[52] U.S. Cl. .................................... 435/123; 435/148; 435/287; 435/288; 435/313
[58] Field of Search ................ 435/123, 148, 150, 157, 435/160, 189, 190

[56] References Cited

U.S. PATENT DOCUMENTS

| | | | |
|---|---|---|---|
| 2,396,900 | 3/1946 | Taggart, Jr. ........................... | 195/28 |
| 3,622,465 | 11/1971 | Orgel et al. ............................ | 195/96 |
| 4,051,020 | 9/1977 | McDonald .......................... | 208/213 |
| 4,106,986 | 8/1978 | Suzuki et al. ........................ | 435/123 |
| 4,187,169 | 2/1980 | Euzen et al. ......................... | 208/157 |
| 4,203,841 | 5/1980 | Shimizu et al. ...................... | 210/205 |
| 4,241,184 | 12/1980 | Patel et al. ............................ | 435/148 |
| 4,247,641 | 1/1981 | Neidleman et al. .................. | 435/123 |
| 4,250,259 | 2/1981 | Hou et al. ............................. | 435/148 |
| 4,284,723 | 8/1981 | Neidleman et al. .................. | 435/123 |
| 4,304,857 | 12/1981 | Brouillard et al. .............. | 435/288 X |

FOREIGN PATENT DOCUMENTS

| | | | |
|---|---|---|---|
| 54-17184 | 2/1979 | Japan .................................... | 435/148 |
| 2019390 | 10/1979 | United Kingdom ................ | 435/148 |
| 2024205 | 1/1980 | United Kingdom ................ | 435/148 |

OTHER PUBLICATIONS

Higgins et al., *Nature*, vol. 286, pp. 561–564 (Aug. 7, 1980).

*Primary Examiner*—Lionel M. Shapiro
*Attorney, Agent, or Firm*—Albert P. Halluin

[57] ABSTRACT

Process and equipment for advancing the oxidation state of a gaseous oxidizable organic substrate through contact with oxygen and a solid state biocatalyst. The process comprises passing through a stationary catalytic bed comprising moist, resting cells exhibiting oxygenase activity, a gaseous, oxidizable organic substrate and a gaseous source of oxygen, until the oxidative state of at least a portion of said substrate is increased, while maintaining the relative humidity in said bed at such a level that said cells remain moist and viable, and while maintaining the temperature in the vapor state. The process uses an oxygenase enzyme as a catalyst, for the incorporation of molecular oxygen directly into a specific organic molecule. The invention is of particular interest for the conversion of propylene to propylene oxide, and similar reactions that are catalyzed by mono-oxygenase enzymes.

24 Claims, 1 Drawing Figure

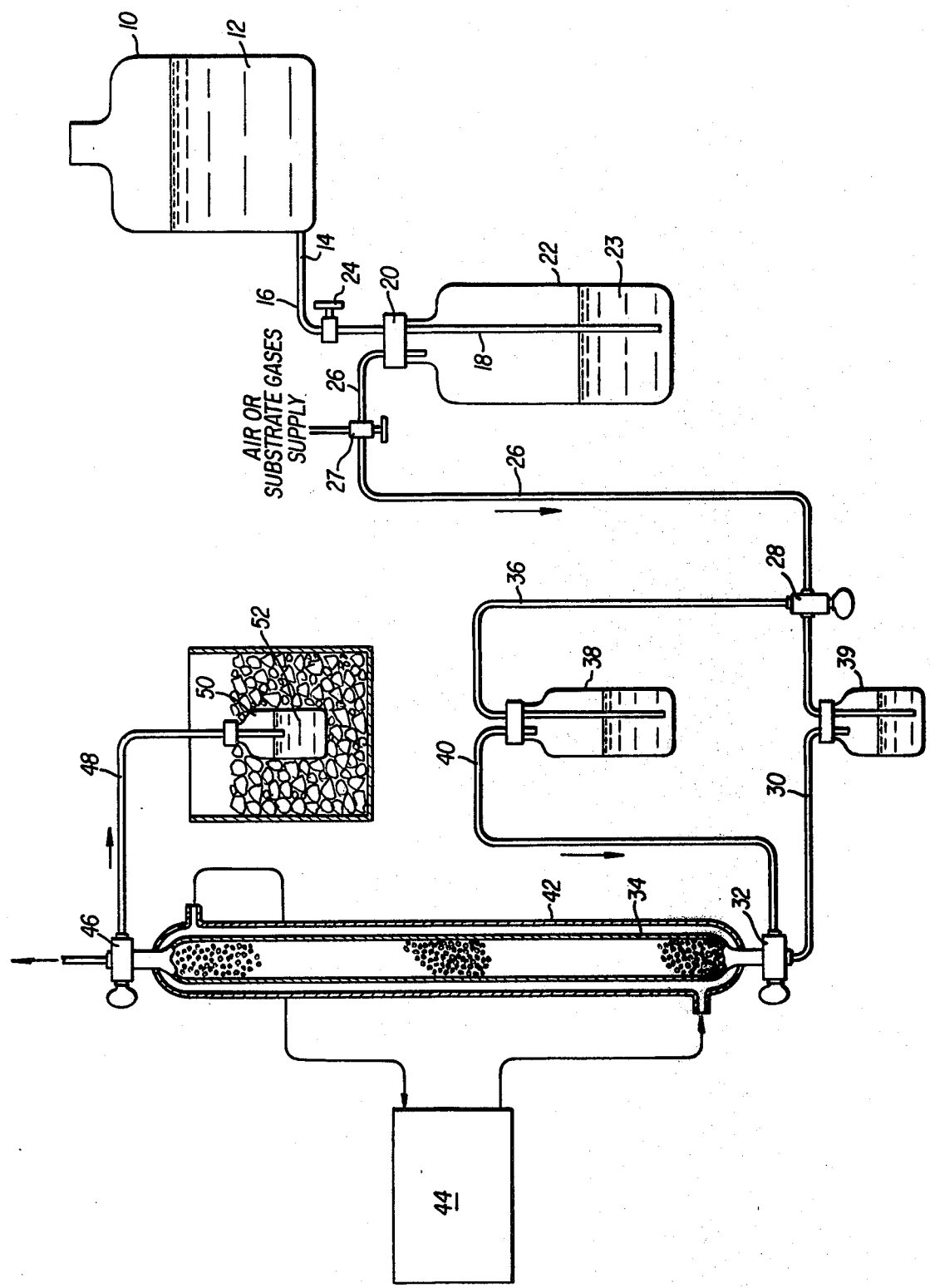

4,348,476

PRODUCTION OF EPOXIDES SUCH AS PROPYLENE OXIDE USING PACKED CATALYTIC BED CONTAINING MOIST RESTING CELLS EXHIBITING OXYGENASE ACTIVITY

INTRODUCTION

This invention relates to a novel process for advancing the oxidative state of a gaseous, oxidizable organic substrate through contact with oxygen and a biocatalyst. More particularly, the invention relates to such a process, that makes use of heterogeneous catalysis, for the production of epoxides from gaseous 1-alkenes, and particularly, for the production of propylene oxide from propylene.

BACKGROUND OF THE INVENTION

An early disclosure of the conversion of hydrocarbons of the paraffinic type by bacterial action is described in U.S. Pat. No. 2,396,900. The method described in that patent converts normally gaseous paraffinic hydrocarbons into heavy, waxy, oxygenated organic compounds by contacting the hydrocarbons in the presence of oxygen with an aqueous nutrient solution inoculated with hydrocarbon consuming bacteria of the group consisting of *Bacillus methanicus* and *Bacillus ethanicus*. The patent describes a continuous process carried out in apparatus similar to a bubble cap tower. The patent speaks of the bacteria consuming the hydrocarbons. It describes what goes on in the patented process as the synthesis, from light hydrocarbons, of oxygenated organic compounds of various molecular weights, from low boiling alcohols to waxy acids, esters and alcohols. When the reaction is permitted to proceed to completion, the product is a predominantly heavy waxy body composed of fatty acids and esters thereof, that may be readily saponified.

A later U.S. Pat. No. 3,622,465, describes a process in which the microorganism *Arthrobacter simplex* utilizes $C_3$–$C_{18}$ straight chain hydrocarbons as a principal source of assimilable carbon and energy to produce single cell protein. The fermentation is carried out, in one embodiment of the invention, on a continuous basis in a sieve plate column, using liquified propane gas as the hydrocarbon.

In my-copending patent application, Ser. No. 160,273, filed June 17, 1980, a continuous process is described comprising establishing a series of separate but interconnected sequential contact zones, flowing a liquid composition comprising a biocatalyst through each of said zones successively from a liquid inlet zone to a liquid outlet zone, flowing an oxidizing gas through each of said zones successively from a gas inlet zone to a gas outlet zone to a gas outlet zone, in intimate, countercurrent contact with the flowing liquid in each of said zones, flowing an organic substrate successively through each of said zones in intimate, reactive contact with said gas and with the liquid composition containing said biocatalyst, and recovering liquid effluent discharged from the liquid outlet zone and gas effluent discharged from the gas outlet zone, the recovered effluents comprising at least some of the oxidizable organic substrate converted to a more advanced state of oxidization. In a preferred embodiment, the gas-liquid contact apparatus in which the process is carried out in a bubble cap tower. In a very preferred mode of practice of the process, $C_2$–$C_4$ n-alkenes and butadiene, particularly propylene, are converted to the corresponding epoxides.

The biocatalytic oxidation reactions, with which the present invention is concerned, have been described in recent literature. In such reactions a biocatalyst is utilized in the presence of oxygen for the conversion of gaseous hydrocarbons into their respective corresponding alcohols, aldehydes, ketones and/or epoxides. Several suggestions have been made in the literature that such processes could be practiced on a continuous basis, but no details were reported for a practical continuous process except for my co-pending patent application Ser. No. 160,273, filed June 17, 1980.

The discovery and isolation of certain methylotrophic microorganisms strains, that grow well under aerobic conditions in a culture medium in the presence of methane as the major carbon and energy source, are reported in U.K. patent application GB 2,018,822 A, published Oct. 24, 1979, which is incorporated herein by reference. These methane-grown microbial cells possess a high content protein. The cells, or enzyme preparations derived from the cells, are said to be useful in converting oxidizable substrates to oxidation products. In particular, $C_1$–$C_6$ alkanes can be converted to alcohols, such as methane to methanol; $C_3$–$C_6$ alkanes can be converted to the corresponding secondary alcohols and methyl ketones; $C_3$–$C_6$ secondary alcohols can be converted to the corresponding methyl ketones; and cyclic hydrocarbons can be converted to cyclic hydrocarbyl alochols, such as cyclohexane to cyclohexanol; and $C_2$–$C_4$ alkenes selected from the group consisting of ethylene, propylene, butene-1 and butadiene, can be converted to 1,2-epoxides.

Cell-free extracts of certain of these hydrocarbon-utilizing microbes, including bacteria and yeasts, contain a nicotinamide adenine dinucleotide (NAD) dependent secondary alcohol dehydrogenase (SADH). This enzyme specifically and stoichiometrically oxidizes $C_3$–$C_6$ secondary alcohols, such as 2-propanol and 2-butanol, to their corresponding ketones.

A process for the epoxidation of $C_2$–$C_4$ alpha olefins and dienes, through the action of a particular kind of biocatalyst in the presence of oxygen, is described in U.K. patent application GB 2,019,390 A, which is incorporated herein by reference. The biocatalyst is a particulate fraction of the microorganism, or an enzyme preparation derived therefrom. The microorganisms are cultivated in a nutrient medium furnishing oxygen and methane or dimethyl ether. The preferred microorganisms are obligative or facultative methylotrophs. Several particularly preferred strains are identified.

In U.K. patent application GB 2,018,772 A, published Oct. 24, 1979, a process is disclosed for the production of ketones or secondary alcohols from $C_3$–$C_6$ alkanes, and ketones from $C_3$–$C_6$ secondary alcohols. The process is conducted under aerobic conditions with resting microbial cells derived from a methyloptophic microorganism, or with an enzyme preparation derived from such cells. The microorganism is one that has been grown under aerobic conditions in a nutrient medium containing a $C_1$-compound and energy source which is an inducer for the enzyme(s) responsible for producing the ketones. The $C_1$ compound may be, for example, methane, methanol, dimethyl ether, methylamine, methyl formate, or methyl carbonate. The term microorganism includes bacteria, protozoa, yeasts, filamentous fungi, and actinomycetes. Yeast cells, grown as referred to, are shown as useful in aerobically converting C$_3$–C$_6$ secondary alcohols. The preparation, isolation and purification of a C$_3$–C$_6$ secondary alcohol dehydrogenase is also described.

The oxidation of alkanes having from 5 to 16 carbon atoms, or of aliphatic alcohols having from 3 to 8 carbon atoms, or cyclic organic compounds, utilizing a biocatalyst, is described in U.K. patent application GB 2,024,205 A, published Jan. 9, 1980, which is also incorporated herein by reference. In the process described in this application, the biocatalyst may be a culture of a methane-utilizing bacterium of the species *Methylosinus trichosporium* or an extract thereof containing a methane oxidizing system.

U.K. patent application 27,886, filed July 4, 1977, and supplemented May 25, 1978, describes the liquid phase oxidation of straight chain alkanes having more than 3 and less than 9 carbon atoms, of alkenes, and of cyclic organic compounds, utilizing as the biocatalyst a culture of a methane oxidizing bacterium or an extract thereof containing a methane oxidizing system. One of the asserted advantages of this process, when enzyme extracts rather than whole cells were used, is said to be the regeneration in situ of cofactors or other biochemical species required for the enzymatic reaction. While the examples describe, and the specification emphasizes, liquid phase oxidation in which a homogenous catalyst is used, one way of carrying out the process that is suggested as a possibility, involves immobilizing such cells on a suitable support material such as glass beads or gel matrix, to form an immobilized enzyme preparation based on the use of cells as the enzyme source. This immobilized enzyme preparation, it is said, may be maintained in a packed or fluidized bed in a suitable contactor. The disclosure of this patent application is also incorporated herein by reference.

These published British patent applications include many references to the pertinent specific literature. A few such items are described below and are incorporated herein by reference.

Hutchinson, Whittenbury and Dalton (J. Theor. Biol., 58 325–335 (1976) "A Possible Role of Free Radicals in the Oxidation of Methane by *Methylococcus Capsulatus*" and Colby and Dalton (J. Biochem., 157, 495–497 (1976) "Some Properties of a Soluble Methane Mono-Oxygenase from *Methylococcus Capsulatus* Strain Bath" reported that ethylene is oxidized by the soluble methane mono-oxygenase from *Methylococcus Capsulatus* Strain Bath. The latter investigators reported that the "particulate membrane preparations" of *Methylococcus capsulatus* Strain Bath did not have methane-oxygenase activity as determined by the bromomethane disappearance test.

Cerniglia, Blevens and Perry, (Applied and Environmental Microbiology, 32 (6) 764–768 (1976) "Microbial Oxidation and Assimilation of Propylene" described the oxidation of propylene by microorganisms to the corresponding alcohols and carboxylic acids.

Most recently, Colby, Stirling and Dalton (J. Biochem., 165, 395–402 (Aug. 1977) "The Soluble Methane Mono-Oxygenase of *Methylococcus capsulates* (Bath) its Ability to Oxygenate n-Alkenes, Ethers, and Alicyclic Aromatic and Heterocyclic Compounds") disclosed that the soluble fraction of *Methylococcus Capsulatus* Strain Bath is a very non-specific oxygenase in that it oxidizes alkanes to alcohols, alkenes to 1,2-epoxides, dimethylether to ethanol and ethanal, styrene to styrene epoxide and pyridine to pyridine N-oxide.

On the basis of $^{18}O_2$ incorporation from $^{18}O_2$ into the cellular constituents of *Pseudomonas methanica*, Leadbetter and Foster (Nature, 184: 1428–1429 (1959) "Incorporation of Molecular Oxygen in Bacterial Cells Utilizing Hydrocarbons for Growth" suggested that the initial oxidative attack on methane involves an oxygenase. Higgins and Quayle (J. Biochem., 118, 201–208 (1970) "Oxygenation of Methane by Methane-Grown *Pseudomonas methanica* and *Methanomonas methanooxidans*") isolated $CH_3^{18}OH$ as the product of methane oxidation when suspensions of *Pseudomanas methanica* or *Methanomonas methanooxidans* were allowed to oxidize methane in $^{18}O_2$ enriched atmospheres. The subsequent observation of methane-stimulated NADH oxidation catalyzed by extracts of *Methylococcus Capsulatus* by Ribbons (J. Bacteriol, 122: 1351–1363 (1975) "Oxidation of C$_1$ Compounds by Particulate Fractions from *Methylococcus Capsulatus*: Distribution and Properties of Methane-Dependent Reduced Nicotinamide Adenine Dinucleotide Oxidane") (methane hydroxylase) and Ribbons and Michalover, (FEBS Lett. 11: 41–44 (1970) "Methane Oxidation by Cell-Free Extracts of *Methylococcus Capsulatus*") or of *Methylomonas Methanica* by Ferenci (FEBS Lett. 41: 94–98 (1974) "Carbon Monoxide-stimulated Respiration in Methane-Utilizing Bacteria") suggested that the enzyme responsible for this oxygenation is a mono-oxygenase.

Recently, methane monooxygenase systems were partially purified from *Methylosinus trichosporium* OB3b (Tonge, Harrison and Higgins, J. Biochem., 161: 333–344 (1977) "Purification and Properties of the Methane Monooxygenase Enzyme System from *Methylosinus trichosporium* OB3b"; and Tonge, Harrison, Knowles and Higgins, FEBS Lett., 58; 293–299 (1975) "Properties and Partial Purification of the Methane-Oxidizing Enzyme System from *Methylosinus trichosporium*") and *Methylococcus Capsulatus* (Bath) (Colby and Dalton, J. Biochem., 171: 461–468 (1978) "Resolution of the Methane Mono-Oxygenase of *Methylococcus Capsulatus* (Bath) into Three Components" and Colby, Stirling and Dalton, J. Biochem., 165: 395–402 (1977) "The Soluble Methane Mono-Oxygenase of *Methylococcus Capsulatus* (Bath) Its Ability to Oxygenate n-Alkanes, n-Alkenes, Ethers, and Alicyclic, Aromatic and Heterocyclic Compounds").

In addition, there are several rather recent literature items of interest, as described below, and each of these is also incorporated herein by reference. These items are described below in chronological order.

Colby and Dalton (*Biochem. J.*, 171, 461–468 (1978)), "Resolution of the Methane Mono-Oxygenase of *Methylococcus Capsulatus* (Bath) into Three Components", describe the fractionation of the enzyme extract into three fractions by ion exchange chromatography. The authors point out that the soluble enzyme extract itself is capable of oxidizing a variety of alkanes, alkenes, ethers and cyclic compounds. Further work was reported by Stirling, Colby, and Dalton (*Biochem. J.*, 177, 361–364 (1979)), "A Comparison of the Substrate and Electron-Donor Specificities of the Methane Mono-Oxygenase from Three Strains of Methane-Oxidizing Bacteria". The authors concluded that similar methane mono-oxygenases were contained in the three bacteria, *Methylosinus Trichosporium*, *Methylococcus capsulatus* (Bath), and *Methylomonas methanica*, based upon studies made with extracts.

Stirling and Dalton (*FEMS Microbiology Letters* 5, 315–318 (1979)), "The Fortuitous Oxidation and Cametabolism of Various Carbon Compounds by Whole-Cell Suspensions of *Methylococcus capsulatus* (Bath)", report that cell suspensions of this organism do not behave in the same manner as extracts, as to oxidizing activity.

More recently, Higgins, Best and Hammond, in a review article (*Nature* 286, 561-4 (1980)), "New Findings in Methane-Utilizing Bacteria Highlight Their Importance in the Biosphere and Their Commercial Potential", presented a survey of recent developments. They point out that as recently as 1965, methanotrophs were regarded, even by most microbiologists, as obscure, uncooperative, perhaps unimportant microorganisms, as evidenced by the fact that, before 1970, only three species had been isolated and well authenticated. Today it is recognized, they say, that these microorganisms include at best two different types of species. Carbon is incorporated into cell material at the oxidation level of formaldehyde by type I species which use the ribulose monophosphate pathway (Quayle cycle) and in type II species, using the serine pathway, as formaldehyde and carbon dioxide. Such bacteria, either as washed suspensions or in culture, will partially oxidize simple substrate analogues, such as ethene, propane and butane, to the corresponding alcohols, aldehydes and fatty acids. It has been shown that carbon monoxide, ammonia and ethene are also oxidized. The authors also state that a surprisingly vast range of multi-carbon compounds, often not closely related to the natural substrates, are oxidized by methanotrophs. Although the capacity to oxidize is said to differ from species to species, the authors state that "the following types of compounds are oxidized by washed cell suspensions: long-chain alkanes (up to at least hexadecane), alkenes, aromatic and alicyclic hydrocarbons, phenols, long-chain and alicyclic alcohols, pyridine, multi-ring compounds and chlorinated aromatic hydrocarbons. In each case only a limited number of products (sometimes only one) are formed as a result of this unexpected activity, showing that there is, nevertheless, some mechanistic specificity. In some cases the products are simply hydroxylated derivatives, suggesting that a reaction analogous to the oxidation of methane to methanol has occurred. Commonly, there is further oxidation of these hydroxylated compounds to yield aldehydes and carboxylic acids."

BRIEF SUMMARY OF THE PRESENT INVENTION

In a preferred embodiment, the invention resides in a process for advancing the oxidation state of a gaseous, oxidizable organic substrate through contact with oxygen and a solid state biocatalyst comprising passing through a stationary catalytic bed comprising moist, resting cells exhibiting oxygenase activity, a gaseous oxidizable organic substrate and a gaseous source of oxygen, until the oxidative state of at least a portion of said substrate is increased, while maintaining the relative humidity in said bed at such a level that said cells remain moist and viable. In another aspect, in the invention is concerned with equipment for practicing this process.

The process and equipment of the invention are particularly useful for carrying out oxidation reactions on gaseous hydrocarbon substrates, containing up to and including 6 carbon atoms per molecule. Generally, the process is based upon the use of an oxygenase enzyme as a catalyst, for the incorporation of molecular oxygen directly into a specific organic molecule. The invention is of particular interest for the conversion of propylene to propylene oxide, and similar reactions that are catalyzed by mono-oxygenase enzymes.

BRIEF DESCRIPTION OF THE DRAWING

The single FIGURE of drawing is a schematic diagram of simple laboratory equipment that can be employed to demonstrate one embodiment of the process of the invention.

DETAILED DESCRIPTION OF THE INVENTION

To practice the process of the invention, a reactor containing immobilized cells is prepared. Microbial cells, in the resting stage, and known to have the desired biocatalytic activity, are formed into a thick paste with buffered solution. The paste is then coated on an inert carrier material. Suitable carriers include porous glass beads, charcoal, activated carbon, dried silica gel, particulate alumina, Ottowa sand, clay, and the like. Care is exercised that the cells remain moist. The immobilized cells prepared in this way are then packed in a suitable reactor, which may simply be a reactor tube. Generally, any suitable reactor may be used that will permit efficient contact between the substrate gases and the cells, while permitting the necessary temperature and humidity control.

Once the biocatalytic bed is prepared in the reactor, it is used by passing the gaseous substrate mixture through the reactor. Generally it is preferred to pass the substrate gas upwardly through the reactor bed, to avoid any settling and compaction of the bed. The reactor bed is maintained at a carefully controlled temperature, slightly higher than the boiling point of the oxidized product, preferably about 5° C. higher. In the case of epoxides of the kind produced by the oxidation process of the invention, generally the temperature within the reactor should be maintained in the range from about 5° C. to about 10° C. above the boiling point of the desired product. In most cases, this means that the operating temperature of the reactor bed will fall in the range from about 15° C. to about 80° C.

The oxidizable substrate may be, for example, a $C_1$–$C_4$ alkane; a $C_2$–$C_4$ alkene or diene, selected from the group consisting of ethylene, propyelene, butene-1, and butadiene; and generally other oxidizable organic substrates that vaporize at a relatively low temperature and that will remain in the gaseous state until condensed from the effluent gas stream. These considerations generally limit the substrate to those molecules having at most 6 carbon atoms, and preferably, not more than 4 carbon atoms. Generally, naturally gaseous substrates are preferred, that is, those substrates that are gaseous at room temperature.

A gaseous source of oxygen is also an essential part of the substrate gas. It may be mixed with the oxidizable substrate gas prior to injection into the reactor, or the gases may be injected into the reactor at the same time but separately, relying upon mixing to occur during passage through the reactor. Preferably, the mixture is made prior to injection into the reactor. The source of oxygen may be air, oxygen itself, or a synthetically prepared mixture of oxygen and nitrogen, for example.

The immobilized cells, that are used in the biocatalyst, are each surrounded by a thin liquid phase. In order to maintain the catalytic activity of the biocatalyst reactor, it is essential that the relative humidity in the reactor be maintained at a level that avoids drying the cells and the liquid phase surrounding them. While this may be accomplished in a variety of ways, including the direct injection of water vapor along with the substrate gases, a preferred technique is simply to pass the substrate gases through a water bath, relying upon them to pick up water vapor and to entrain water droplets in doing so. Generally the relative humidity within the reactor should be maintained in the range from 50% to 100%, and preferably from 70% to 100%.

The catalytic bed in the reactor may be a dynamic bed or a stationary bed, the latter being preferred. When a dynamic bed is employed, the oxidation reaction and the regeneration of the catalyst can, if desired, be carried out continuously, by using separate reactors for each of these separate reactions, respectively.

Product recovery can be accomplished by chilling the effluent stream to condense the product. The remaining gases from the effluent stream may be recycled. If air is used as the source of oxygen, and if recycling of the effluent gas remaining after condensation of the product is practiced, it may be desirable to inject supplemental oxygen directly into the gas supply to the reactor bed or into the recycling gases, in order to maintain the oxygen level at a sufficiently high value for good reactivity.

After a period of use, the biocatalytic activity of the reactor bed may drop off. If the cells remain viable, the biocatalytic activity can be restored at least in part by passing a suitable hydrocarbon, preferably a $C_1$ source, such as methanol vapor, for example, upwardly through the reactor bed for a long period of time.

Referring now in detail to the drawing by numerals of reference, the following description applies to equipment for practicing one preferred embodiment of the invention wherein the gaseous, oxidizable organic feed stock is gaseous propylene, which is converted through the action of a biocatalyst in a packed bed to propylene oxide. The numeral 10 denotes a jar containing a supply of water 12. The jar 10 is provided with a discharge outlet 14 at its lower end. This discharge outlet 14 is connected through a valve 24 to a glass tubing 18 that is mounted through an opening in a stopper 20 to project into another bottle 22 containing a supply of water 23. The tubing 18 extends down into close proximity with the bottom of the bottle 22.

A flexible tubing 26 is mounted to extend through a second opening in the stopper 20 in the bottle 22, and is connected to three-way stopcocks 27 and then 28. The third port of this stopcock 27 is connected to supply sources of air or substrate gases. A second port of this stopcock 28 is connected through another piece of flexible tubing 30 to a water bottle 39, the lower end of the tubing 30 projecting far enough into this bottle 39 to be well below the water level. A second piece of tubing 41 connects the vapor space at the upper end of the water bottle 39 to one port of another three-way stopcock 32, a second port of which is connected to the lower, inlet end of a packed reactor 34.

To provide a regeneration system for the biocatalyst in the packed bed reactor 34, the third port of the stopcock 28 is connected through a length of tubing 36 to a methanol bottle 38, the lower end of the tubing 36 projecting far enough into this bottle to be well below the level of the supply of methanol in the bottle. A second piece of tubing 40 connects the vapor space at the upper end of the methanol bottle to the third port of the stopcock 32.

The packed reactor 34 is provided with a heat exchange jacket 42, that is connected to a temperature control device, indicated generally by the the numeral 44, for circulating heating liquid, for example, through the jacket 42.

At its upper end, the reactor 34 is connected to one port of another three-way stopcock 46. A length of tubing 48 is connected to a second port of this stopcock 46, to direct effluent from the reactor into a chilled condenser 50. This condenser 50 may be kept at a low temperature by being disposed in a bed of chopped ice 52. The third port of the stopcock is connected to a source of low pressure, such as a vacuum pump (not shown). The pressure of substrate gases within the reactor 34 can be adjusted to a desired level, by adjusting the setting of the stopcock valve 46 and the elevation of the jar 10 relative to the bottle 22.

For laboratory purposes, the condenser 50 may be more elaborate than is shown or indicated schematically in the drawing, and in particular, may present a travel path of much greater length than that as shown in the schematic diagram drawing. In addition, in practice there are unconverted gaseous materials in the effluent, and these may either be vented to the atmosphere or recycled through the packed reactor; neither of these expedients is shown, in order to keep the drawing simple.

To illustrate the use of this equipment to practice certain embodiments of the invention, several demonstrations of the invention are described in the following examples. In these examples and elsewhere throughout the specification, all parts and percentages are by weight unless expressly stated to be otherwise, and all temperatures are expressed in degrees Celsius.

EXAMPLES

Laboratory Scale Demonstrations of the Production of Propylene Oxide

In these demonstrations, the equipment schematically shown in the drawing was used.

To prepare the packed bed reactor, a cell paste was prepared from a mixture of cells and a 905 M phosphate buffer solution, pH 7.0. The cells were the harvest from methane-grown *Methylosinus trichosporium* (OB3b, NRRL B-11,196).

The carrier material selected was a sufficient quantity of glass beads to fill the small laboratory reactor. The glass beads were porous and had a maximum diameter of about 2 mm. They were immersed in the cell paste, and the cells became bound to the glass beads by this simple technique. The cells adhered in a thin layer, without the need for any chemical manipulation or other special steps. The coated beads were then packed into the glass reactor, which was 15 cm. in length and one cm. in inner diameter. As shown in the drawing, this reactor was equipped with a jacket for circulating water, as a temperature controlling means.

A gaseous substrate mixture was prepared by mixing equal parts by volume of propylene and oxygen inside the bottle 22 through displacing the water in the bottle 22 and pushing it up into the glass jar 10.

The bottles 38 and 39 were loaded with methanol and water respectively. Both bottles were immersed in a 40° C. water bath to facilitate vaporization of the liquids inside the bottles, respectively.

Fresh ice 52 was placed around the condenser 50, and the heat exchange unit 44 was activated and operated for a period of time to adjust the temperature of the packed reactor bed to about 40° C.

The reactor 34 was evacuated and the reactor was then filled with the gaseous substrate mixture. The reactor was then permitted to stand for five minutes of preincubation at 40° C.

The substrate gas mixture was then introduced continuously into the reactor at a flow rate of about one ml. per minute, with the temperature being maintained at about 40° C. The relative humidity inside the reactor was maintained at about 70%.

The product, propylene epoxide, was recovered as a condensate in the condenser. This reaction was continued for seven hours, during which the production of propylene oxide was observed to occur at an essentially constant rate of about 18 micromoles per hour. After seven hours of continuous operation, the rate of production of propylene oxide was observed to become slower, indicating some loss of activity by the biocatalyst. Possibly, this loss of activity was caused by the depletion of the reducing power (or co-factor NADH) of the cells.

After ten hours of operation, product production essentially stopped. After 12 hours of operation, the introduction of the substrate gas mixture was discontinued.

The substrate gas inside the bottle 22 was then replaced with air. This air was then caused to bubble through the methanol in the bottle 38, and then passed through the reactor bed, carrying methanol vapor with it. The air was bubbled through the methanol, and then into the reactor bed, at a rate of about five ml. per minute. This was continued for 30 minutes, during which the reactor temperature was maintained at about 40° C. At the end of that time, the air flow was discontinued. The air inside the bottle 22 was again replaced with substrate gases, and the reaction was resumed.

The production of propylene oxide immediately began again and was continued for an additional period of four hours. The rate of production was slightly below that observed during the first seven hours of operation of the reactor bed. During the initial four hours of operation of the reactivated biocatalyst, about 48 micromoles of propylene oxide were produced, for an average rate of production of about 12 micromoles per hour.

The procedure just described was repeated except that the biocatalyst was prepared from a cell paste of cells of *Methylococcus capsulatus* M1 (NRRL B-11,219). During the first seven hours of operation of the reactor, the rate of conversion of propylene to propylene oxide was about 15 micromoles per hour. After regeneration with methanol, the conversion of propylene to propylene oxide started again at a rate of 4 micromoles per hour.

Similar results are obtained when, in preparing the biocatalyst, the cells used are those of any of the microbes that exhibit growth when cultured in a medium in which the nutrient and growth medium is a $C_1$–$C_4$ gaseous alkane. These microorganisms may be bacteria, yeast, fungi, and the like.

GENERAL

Where the substrate is an alkene or diene selected from the group consisting of ethylene, propylene, butene-1, isobutylene, and butadiene, the cells utilized in making the immobilized cell biocatalyst are those of a somewhat select group of microorganisms, cultivated in a nutrient medium containing a C-1 compound. The C-1 compound ordinarily is methane or dimethyl ether. The group of microorganisms are those that belong to the genera Methylosinus, Methylocystis, Methylomonas, Methylobacter, Methylococcus or Methylobacterium. Preferably, the microorganism species selected for use is one selected from the group of species consisting of: *Methylosinus trichosporium, Methylosinus sporium, Methylocystis parvus, Methylomonas methanica, Methylomonas albus, Methylomonas spectobacterium, Methylomonas agile, Methylomonas rubrum, Methylomonas rosaceus, Methylobacter chroocuccum, Methylobacter bovis, Methylobacter capsulatus, Methylobacter vinelandii, Methylococcus capsulatus, Methylococcus minimus* and *Methylobacterium organophilum*.

Most preferably, the cells selcted for this purpose are strains having the designations, respectively:

*Methylosinus trichosporium* (NRRL B-11,196);
*Methylosinus sporium* (NRRL B-11,197);
*Methylocystis parvus* (NRRL B-11,198);
*Methylomonas methanica* (NRRL B-11,199);
*Methylomonas albus* (NRRL B-11,200);
*Methylobacter capsulatus* (NRRL B-11,201);
*Methylobacterium organophilum* sp nov. (ATCC 27,886);
Methylomonas sp AJ-3670 (FERM P-2400);
Methylococcus sp (NCIB Accession No. 11,083); or
Methylomonas sp (NCIB Accession No. 11,084).

Most commonly, the process of the invention will be practiced to convert gaseous $C_2$ to $C_4$ alkenes into such oxidized products as, for example, ethylene oxide, propylene oxide, epoxybutane, epoxybutene, and epoxyisobutylene. Gaseous alkanes may also be oxidized. Depending upon the conditions employed, and the particular microorganism selected, methane oxidized into methanol and formaldehyde. Also, acetone, 2-butanone, 2-pentanone, and the like can be produced. Most commonly, the $C_1$ to $C_4$ alkanes will will be oxidized to 1- or 2-alcohols, to aldehydes, or to methyl ketones.

Gaseous alkanes and alkenes can also be converted into their respective corresponding alcohols and aldehydes, depending upon the conditions selected for the reaction.

Some of the underlying scientific information with respect to the enzymatic activity of the cells of *Methylococcus capsulatus*, strain Bath, may be found in the article by Colby et al., *J. Biochem.*, 165, 395–402 (1977), referred to above. As that article points out, the methane mono-oxygenase of *Methylococcus capsulatus* strain Bath is a multi-enzyme that catalyzes the NADH- and oxygen-dependent oxidation of methane to methanol. As that article reports, the methane mono-oxygenase is effective for the oxidation of several derivatives of methane. These include chloromethane, bromomethane, and other derivatives that are generally not gaseous at room temperature. The present invention finds its greatest usefulness in connection with the oxidation of compounds that are gaseous at room temperature, or if not, that become gaseous at temperatures below about 50° C.

This invention finds its greatest usefulness with $C_1$–$C_4$ alkanes, all of which have boiling points below 0° C. While the invention is also useful in connection with the oxidation of n-pentane, its boiling point of 36° C. makes it a little more difficult to handle in the process of the invention, to maintain it in the gaseous state, and accordingly the economics are less attractive. The same considerations apply to hexane, with its boiling point of 69° C.

The term "alkanes" should be understood to include cyclic alkanes such as, for example, cyclopropane and cyclobutane, as substrate materials that are useful in the practice of the invention. These materials have boiling points of about −33° C. and 11° C., respectively, and accordingly can be utilized conveniently as gaseous substrates. Cyclopentane has a boiling point of about 49.5° C., and accordingly, while it can be used as a substrate, it does have the practical disadvantages mentioned above. Cyclohexane, with its boiling point of 81.4° C., is at the upper limit of the temperature range of the process and is marginally useful per se, but can be a useful component in a gaseous mixture.

Similarly, the $C_1$ to $C_4$ alkenes all have boiling points below 0° C., and accordingly are gaseous at room temperature. They are also useful for oxidation in the process of the invention. The C-5 alkenes, on the other hand, have boiling points in the 20° C. to 30° C. range, generally, and while less attractive for use for that reason, are useful, whereas the hexenes, with boiling points in the 60's, are not preferred feedstock material.

While the catalyst support materials or carriers that have been identified as useful are generally inert materials, and primarily inorganic, the essentials for the carrier are that it be inert, capable of accepting the adherence thereto of a cell paste, or of adsorbing cells thereto, or, in the case of porous materials, perhaps of binding the cells by lodging in the porous structure. In addition, the carrier must be sufficiently strong to permit its use in a column of reasonable size, to permit practical application of the process. The basic functions of the carrier are to support the cells and to improve mass transfer.

The present process affords several advantages. First, the biocatalyst bed may be stationary, so that the individual cells are not subjected to physical abuse, and can be reactivated when their enzyme activity is spent or decreased.

Another very important advantage is that the process eliminates water treatment problems. That is, both pretreatment of process water and the treatment of residual waste water are not entailed in the use of the process. The only liquid phase present is a small quantity of moisture that surrounds each cell, together with the small quantity of water in the water bath used in connection with humidity control in the reactor bed. Little water is involved in the oxidation process.

In reactivating the cells when the activity rate drops off, methane and all of its metabolites may be used. The use of a gaseous compound for regenerating the catalyst, is still another very advantageous and unusual feature of the present invention.

While the invention has been described in connection with certain specific embodiments thereof, it will be understood that it is capable of further modifications, and this application is intended to cover any variations, uses, or adaptations of the invention following, in general, the principles of the invention and including such departures from the present disclosure as come within known or customary practice within the art to which the invention pertains and as fall within the scope of the appended claims.

What is claimed is:

1. A process for advancing the oxidation state of a gaseous, oxidizable organic substrate through contact with a gaseous source of oxygen and a biocatalyst comprising:

passing through a packed catalytic bed comprising moist, resting cells exhibiting oxygenase activity a gaseous, oxidizable organic substrate and a gaseous source of oxygen until the oxidative state of at least a portion of said substrate is increased, while maintaining the relative humidity in said bed at such a level that said cells remain moist and catalytically active until spent.

2. The process of claim 1 wherein said gaseous organic substrate is a $C_1$ to $C_4$ alkane or a $C_2$ to $C_4$ alkene, and the temperature of the bed is maintained in the range from about 15° C. to about 80° C.

3. A process according to claim 2 wherein said catalytic bed comprises a mass of catalytic materials produced by applying a paste of cells and water to particles of an inert carrier.

4. The process of claim 3 wherein said carrier particles are porous glass beads.

5. The process of claim 3 wherein said carrier particles are silica particles.

6. The process of claim 3 wherein the carrier particles are not over 2 mm. in their largest dimension.

7. The process of claim 3 wherein the cells are those of a methylotrophic microorganism.

8. The process of claim 7 wherein the cells are obtained by culturing on a C-1 compound.

9. The process of claim 7 wherein said cells are obtained by culturing on a lower alkane.

10. The process of claim 1 including the step of restoring at least a part of spent catalytic activity of the cells in situ.

11. The process of claim 10 wherein the step of restoring catalytic activity comprises blowing a gaseous, nutrient carbon-containing compound and a gaseous source of oxygen through said bed.

12. The process of claim 11 wherein said nutrient carbon-containing compound is methane or one of its metabolites.

13. The process of claim 11 wherein said nutrient carbon-containing compound is methanol.

14. The process of claim 10 comprising restoring spent catalytic activity by restoring the reducing power of the cells.

15. The process of claim 1, 2, 3 or 7, comprising recovering the oxidized substrate by chilling the effluent gaseous stream to condense the oxidized substrate product.

16. The process of claim 15 including the step, after condensing the product from the effluent, of recycling residual gas through the process.

17. A process for advancing the oxidation state of a gaseous, oxidizable organic substrate through contact with a biocatalyst and with a gaseous source of oxygen comprising:

passing through a packed biocatalytic bed comprising moist, resting cells exhibiting oxygenase activity a gaseous source of oxygen together with a gaseous, oxidizable organic substrate selected from the group consisting of saturated and unsaturated compounds being not more than four carbon atoms, at a temperature in the range from about 15° C. to about 80° C., while maintaining the relative humidity conditions in the bed so that the cells remain moist and catalytically active, maintaining the reactor and operating temperature at a temperature level within said range at which the effluent, containing oxidized substrate, remains gaseous, and passing the gaseous effluent through a chilled condenser that converts the oxidized product to a liquid while any unoxidized substrate remains gaseous.

18. The process of claim 17 including recycling any unoxidized substrate gas through the process.

19. The process of claim 1, 2, 3, 7, 10 or 17 wherein the microorganism is from the group of genera consisting of Methylosinus, Methylocystis, Methylomonas, Methylobacter, Methylococcus, and Methylobacterium.

20. The process of claim 19 wherein said microorganism is a species selected from the group consisting of *Methylosinus trichosporium, Methylosinus sporium, Methylocystis parvus, Methylomonas methanica, Methylomonas albus, Methylmonas spectobacterium, Methylomonas agile, Methylomonas rubrum, Methylomonas rosaceus, Methylobacter chroocuccum, Methylobacter bovis, Methylobacter capsulatus, Methylobacter vinelandii, Methylococcus capsulatus, Methylococcus minimus* and *Methylobacterium organophilum.*

21. The process of claim 20 wherein the microorganism is a strain selected from the group consisting of:
*Methylosinus trichosporium* (NRRL B-11,196);
*Methylosinus sporium* (NRRL B-11,197);
Methylocystis parvus (NRRL B-11,198);
*Methylomonas methanica* (NRRL B-11,199);
*Methylomonas albus (NRRL B*-11,200);
*Methylobacter capsulatus* (NRRL B-11,201);
Methylobacterium organophilum sp *nov.* (ATCC 27,886);
Methylomonas sp AJ-3670 (FERM P-2400);
Methylococcus sp (NCIB Accession No. 11,083); or
Methylomonas sp (NCIB Accession No. 11,084).

22. The process of claim 1, 2, 3, 7 or 17 comprising maintaining the humidity by passing the gaseous substrate and the gaseous source of oxygen through a body of water before passing them through said bed.

23. The process of claim 1, 2, 3, 7 or 17 wherein the oxidizable organic substrate is propylene and the oxidized product produced is propylene oxide.

24. A process for converting propylene to propylene oxide through contact with a gaseous source of oxygen and a biocatalyst comprising:
passing gaseous propylene through a packed catalytic bed comprising inert solid carrier particles having disposed thereon moist, resting cells exhibiting enzymatic activity capable of converting the propylene to propylene oxide in the presence of oxygen, and simultaneously passing through the packed bed with the propylene a gaseous source of oxygen, maintaining the gaseous materials in contact with the bed until at least some of the propylene is converted to propylene oxide, while maintaining the relative humidity of the propylene and of the gaseous source of oxygen at such a level that said cell remain moist,
maintaining the bed at a temperature in the range from about 15° C. to about 80° C.,
said cells being those of a methane-grown microorganism from the group of genera consisting of Methylosinus, Methylocystis, Methylomonas, Methylobacter, and Methylobacterium, and
recovering the propylene oxide from the gaseous effluent by chilling the effluent to condense the propylene oxide.

* * * * *